US012594098B2

(12) United States Patent
Mehta et al.

(10) Patent No.: US 12,594,098 B2
(45) Date of Patent: Apr. 7, 2026

(54) POSTEROLATERAL INSTRUMENTATION TREATMENT SYSTEM AND METHODS

(71) Applicant: The Board of Trustees of the University of Illinois, Urbana, IL (US)

(72) Inventors: Ankit Mehta, Chicago, IL (US); Philip Ostrov, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 891 days.

(21) Appl. No.: 17/617,697

(22) PCT Filed: Jun. 17, 2020

(86) PCT No.: PCT/US2020/038127
§ 371 (c)(1),
(2) Date: Dec. 9, 2021

(87) PCT Pub. No.: WO2020/257276
PCT Pub. Date: Dec. 24, 2020

(65) Prior Publication Data
US 2022/0296280 A1     Sep. 22, 2022

Related U.S. Application Data

(60) Provisional application No. 62/863,089, filed on Jun. 18, 2019.

(51) Int. Cl.
| | |
|---|---|
| *A61B 17/70* | (2006.01) |
| *A61B 17/88* | (2006.01) |
| *A61M 1/00* | (2006.01) |

(52) U.S. Cl.
CPC ...... *A61B 17/7002* (2013.01); *A61B 17/7098* (2013.01); *A61B 17/8822* (2013.01); *A61M 1/85* (2021.05); *A61M 2210/1003* (2013.01)

(58) Field of Classification Search
CPC ........................ A61B 17/7017; A61B 17/7002
See application file for complete search history.

(56) References Cited

U.S. PATENT DOCUMENTS

| | | | |
|---|---|---|---|
| 9,173,692 B1 | 11/2015 | Kaloostian | |
| 2003/0083662 A1* | 5/2003 | Middleton ......... | A61B 17/7098 606/92 |

(Continued)

OTHER PUBLICATIONS

International Search Report and Written Opinion mailed Oct. 8, 2020 for International Application No. PCTUS2020/038127, 18 pages.

*Primary Examiner* — Tessa M Matthews
(74) *Attorney, Agent, or Firm* — McDonnell Boehnen Hulbert & Berghoff LLP

(57) ABSTRACT

A method for controlled delivery of fluids to the exterior of bone and surrounding tissue of a patient includes providing a cannulated bone rod. The method further includes creating an aperture in the skin of a patient and fixating the rod along bones or bone fragments using a spinal fixation system through the aperture. A spinal fixation system includes a bone screw having a longitudinal access and a bone rod configured to connect the bone screw to at least one additional bone screw. The bone rod is lateral to the longitudinal axis. The method further includes the steps of providing a fluid source, coupling the fluid source to the bone rod, and delivering a fluid from the fluid source into the bone rod. An additional method includes using the fixation system as a point of drainage for the posterolateral fusion site.

19 Claims, 8 Drawing Sheets

(56) References Cited

U.S. PATENT DOCUMENTS

| 2010/0030135 A1 | | 2/2010 | Mitchell | |
|---|---|---|---|---|
| 2010/0268279 A1 | * | 10/2010 | Gabelberger | A61B 17/7041 |
| | | | | 606/278 |
| 2011/0112579 A1 | * | 5/2011 | Brazil | A61B 17/7004 |
| | | | | 606/279 |
| 2014/0188172 A1 | * | 7/2014 | Nichols | A61B 17/7002 |
| | | | | 606/278 |
| 2020/0253645 A1 | * | 8/2020 | Manwill | A61B 17/7082 |

* cited by examiner

140

122

122

120

150

A

A

102

130

100

A (10:1)

B-B
(11:1)

Figure 5c
Figure 5b
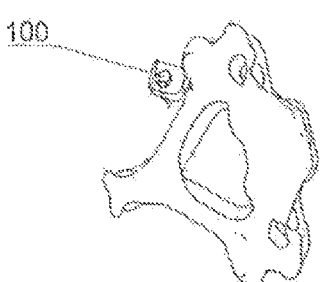
Figure 5a
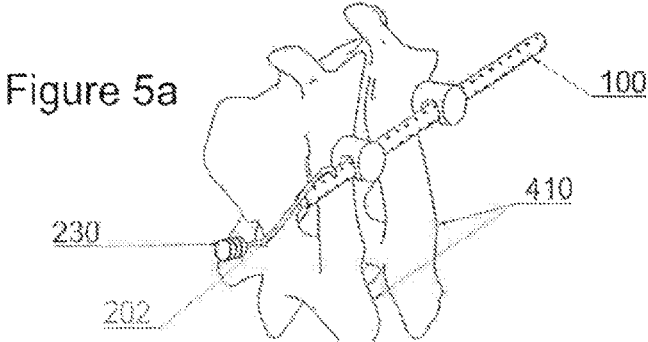

710

202

602

702

POSTEROLATERAL INSTRUMENTATION TREATMENT SYSTEM AND METHODS

FIELD OF THE DISCLOSURE

The present disclosure sets forth systems and methods for selectively providing one or more local treatments within a fixation construct region, such as across one or more segments of the spinal column for example. More specifically, systems configured in accordance with the principles herein can be configured to facilitate one or more intervention methods to a surgical site, including medical treatment delivery and drainage, for example.

BACKGROUND OF THE DISCLOSURE

The motion and support functions of the spine, in combination with the many interlocking parts and nerve roots associated with the spinal column can result in back pain due to various reasons. Such back pain may result from the degeneration of discs due to age, disease, or injury. Further, vertebral bodies may be compromised due to disease or defect, such as a tumor, or injury, such as a fracture.

The spinal column is comprised of twenty-six interlocking vertebrae. The vertebrae are separated by discs. The spine provides load-bearing support for one-half of the body's mass and it protects the nerves of the spinal column. The combination of the vertebrae and discs at each vertebral segment allows for motion of the spine, in particular, flexing, rotation, lateral bending, and extension.

Spinal fusion or fixation surgery is one way to treat back pain. Further, spinal fusion or fixation may be used to correct an abnormal curvature of the spine or stabilize the spine due to injury or disease affecting one or more discs or vertebrae. Additionally, certain pathologies within the spinal canal require destruction of the bony elements of the spine for proper treatment, and thus leave the spine weakened.

In a spinal fusion procedure, two or more adjacent vertebrae in the spine are fused together. The fusion is typically accomplished by the utilization of spinal instrumentation including one or a pair of rods that are connected to several vertebrae via bone screws. The rods may be aligned along the periphery of the vertebrae, and are typically used to maintain the alignment of the bones to provide spinal stability and promote a bony fusion along the posterolateral recesses. During these procedures, bone graft may be pasted onto the bone rod and posterolateral bony structures in hopes of establishing this bony fusion.

Many fixation devices are currently available. Spinal fixation components vary depending on the system being utilized but typically include pedicle screws that are inserted through the pedicle and into the vertebral body. The pedicle screws are typically attached to one another by a linking device, such as a rod, that extends vertically along the row of pedicle screws that are inserted. Several coupling systems are known in the art that are used for coupling the pedicle screws to the linking device, which is oriented parallel to the spinal column. Typically two columns of pedicle screws and linking devices are used, one on each side of the spinal column.

After installation, the two linking devices may be attached to one another to provide additional stabilization of that portion of the spine. Because of anatomical variations, the pedicle screws that are fixed to one another in a spinal fusion procedure may not be in longitudinal alignment with one another. Accordingly, spinal fixation systems utilizing a rod strive to allow some variability in the placement of the pedicle screws while still accomplishing the goal of fixation with a single rod along the pedicle screws.

The rod used for fixation can also be manipulated (cut or bent) intraoperatively or pre-operatively to better fit the alignment of the patient's spine and properly link all of the screws. In addition, disease, trauma and tumors affecting bones, such as vertebrae, often require delivery of treatment agents, including therapeutic agents, diagnostic agents and imaging agents to the area of the bone.

Unfortunately, known bone implant devices, in particular known spinal implants, associated with bone stabilization or bony fusion procedures are not simple to recover from. Further, failure to deliver interventions both intraoperatively and post operatively as needed can negatively impact a patient's return to mobility following a spinal procedure. Unfortunately, mobility milestones are clinically significant to optimizing post-operative success for spinal procedures.

SUMMARY

In accordance with the principles of the present disclosure, a system including one or more customizable bone rods and at least one selectively removable treatment device is set forth. The one or more bone rods can incorporate custom fenestrations selectively connectable to the removable treatment device in a desired treatment location along at least a portion of the bone rod. A portion of the bone rod can form an interior hollow. The interior hollow can connect any group of custom fenestrations. Alternatively, fenestrations can be provided along a length of the bone rod, and one or more fenestrations along the bone rod can be selectively cannulated with the removable treatment device to form a pathway for treatment, whereby either a treatment substance can be delivered into any fenestration and excreted through all other bone rod fenestrations and openings, or fluid can be drawn from a surgical site.

In accordance with the principles herein, the system can be configured to combine bone stabilization, repair and/or replacement along with treatment agent delivery and/or fluid removal.

Systems constructed in accordance with the principles herein are capable of selective and/or controlled delivery of a substance to a surgical site, such as a posterolateral fusion site, to address a number of clinical needs, including but not limited to prophylaxis, infection treatment, pain management, bone growth, seroma formation, improved mobility, and other uses of medicant injection that reduce postoperative complications, recurrent surgical intervention, disease progression, and systemic toxicity.

In addition, systems constructed in accordance with the principles herein can be customized based on delivery location and amount of the substance(s) delivered during the course of an operation, once the bone rod is in place, for example, as well as after the operation is finished.

Further, systems constructed in accordance with the principles herein can be configured to facilitate stable, localized drain sites via selectively connectable components. In an embodiment, the drain sites can be accessible subcutaneously, such as at the fusion site or other suitable location, for the reduction or prevention of postoperative infections and reduction in complications related to cannula displacement and fluid accumulation, such as an infection and seroma formation.

In an embodiment, a posterior instrumentation system, whereby two or more vertebral bodies may be held in a fixed spatial relationship with respect to each other, can include two vertical bone rods, connected by pedicle screws. Selective delivery of a substance at or near the posterolateral fusion site and or fracture interface of a broken bone can be achieved with a system configured in accordance with the principles herein, for example. In such a case, the desired positions of bone rod fenestrations can be configured to align with or match the broken bone location, which may not be known until after the bone rod has been disposed along the bones. To this end, multiple exemplary embodiments are set forth herein to demonstrate the flexibility for treatment delivery during and after a surgical procedure.

For example, readjustment or realignment of the bone rod during an initial spinal fixation procedure can provide options to change and customize directed delivery of a treatment substance at a later point in time based on the changing post-surgical needs of the patient. The system of the present disclosure thus allows selectively maintaining one or more substance delivery and/or removal pathways to selectable bone rod fenestrations within one or more bone rods to which substance delivery and/or removal is desired.

In an embodiment the system can include one or more hollow interior chambers, or fluid chambers, which may serve as a fluid pathway for one or more substances to be delivered to the bone and surrounding tissue of the posterolateral fusion. Reservoirs may be connectable to a removable treatment device to deliver treatment substances to the fluid chamber. To this end, the removable treatment device can include flexible tubing and a suitable connector attachable to or integrally formed with the flexible tubing, for example.

Certain embodiments of the present disclosure may further comprise a pump for facilitating the delivery of the one or more substances to the posterolateral fusion. Such pumps can, for example, aid in the continuous or regulated flow of a fluid into the bone rods for delivery to the desired location. Different medicants may be delivered into the bone rod synchronously or in serial, through the same cannula or through different cannulas, continuously or intermittently. In one embodiment, for example, a medicant such as chemotherapy may be delivered through one bone rod to the fusion site while another medicant such as antibiotics may be delivered to the fusion site through the bone rod on the contralateral side. Regulated fluid delivery can serve to decrease the incidence of subcutaneous tissue infections, decrease the incidence of seroma formation and heterotopic ossification, reduce the recurrence of spinal tumors, reduce patient post-operative pain, and increase the rate of bony fusion, for example.

In other embodiments, a syringe can be selectively inserted into or selectively attached to the removable treatment device. The syringe can selectively or continuously deliver fluid into the tubing of the removable treatment device. A connector of the removable treatment device can be selectively attached to one or more of the bone rod fenestrations. Alternatively, fluid can be delivered directly into one of the bone rod fenestrations, and the fixation—rod can be configured to removably secure tubing thereto. In certain embodiments, connectors configured in accordance with the principles herein can include two or more annular ridges or other structural members configured and adapted to provide a secure yet removable connection to any portion or all of the bone rod.

In accordance with the principles herein a method for manufacturing a treatment system, including drainage, for a surgical site is set forth. The method can include the step of configuring a removable treatment device to include at least one cannula, or flexible tubing, and one or more connectors. The one or more connectors can be customized for removable insertion into one or more bone rod fenestrations. The one or more bone rod fenestrations can be formed in any suitable diameter and geometry, in accordance with the principles herein. The removable treatment device can facilitate the removal of fluid during or after a medical procedure, wherein fluid can be drawn from a drainage pathway. Such fluid can contain Serosanguineous fluid, Proteinaceous fluid, Pathogens, Inflammatory fluids, irrigation fluid, antibiotic fluid, and the like as well as any previously delivered fluids by a system constructed in accordance with the principles herein.

In an exemplary embodiment, the treatment system can be manufactured to form removable or fixed connections to a negative pressure device or gravity based drainage system to facilitate fluid removal through flexible tubing into an external reservoir. Systems constructed in accordance with the principles herein can decrease the need for surgical debridement of a wound, and further decrease the rate of postoperative infections by both draining the site and providing a delivery mechanism for substances to treat a selected region. Additionally, reduced incidence of cannula displacement for drainage within the posterolateral fusion procedure may reduce the incidence of complications such as infection or seroma formation, for example.

In an exemplary embodiment, the system can be configured to facilitate long-term delivery of fluids to the exterior of bone and/or surrounding tissue of a patient by including a cannulated bone rod. An aperture can provide access through the tissue superficial to the fusion site of a patient in order to fixate the rod along bones or bone fragments when using the treatment system. Certain surgical tools, such as a trocar or other tools known to those skilled in the art, may provide better access to the fusion site through the aperture. A treatment system can include a bone screw having a longitudinal access and a bone rod configured to connect the bone screw to at least one additional bone screw. The bone rod can be disposed lateral to the longitudinal axis. A fluid source can be selectively coupled to the bone rod, in accordance with the principles herein, to enable delivering a fluid from the fluid source into the bone rod.

The treatment system can further serve as a point of drainage for a surgical site. The exemplary systems and methods herein refer to spinal fusion procedures, but also contemplate additional uses and/or procedures that improve patient access and treatment in accordance with the principles herein. For example, the systems and methods described herein could be applied to fixate one or more bones of an arm, a leg, or another body part following traumatic breakage of the bone(s), cutting or other surgical manipulation of the bone(s), or to provide some other benefit via fixation of two or more bones or portions of bones together via one or more bone screw(s) and/or bone rod(s).

To date a higher rate of post-operative infections are believed to occur after spinal fusion surgeries compared to other spinal surgeries. These infections require surgical debridement of the wound, and would therefore increase surgical complication rates at a hospital. There is a significant portion of bony fusions with a rod interphase that fail to form properly, causing a pseudarthrosis. Further, localized delivery of chemotherapy, antibiotics, osteoinductive factors, analgesics to this area of the body can be difficult.

Systems and methods constructed in accordance with the principles herein provide a solution to address these specific issues associated with spinal fusion surgeries, while enabling a wide range of treatment options for other patient care needs. Numerous benefits can be derived in accordance with the principles herein, such as the improved mobility and prognosis of the patient due to improved post-operative comfort, among others. Other benefits can include, but are not limited to, reducing supratherapeutic levels of osteoinductive factors that can increase rates of postoperative complications such as heterotopic ossifications and seromas, for example. Direct delivery with micro infusion pumps may reduce the rate of these complications. Also, muscle pain after spinal surgery can limit a patient's mobility for proceeding days, which can lengthen recovery time. Directed delivery of analgesics to the posterolateral fusion site may reduce this pain and thus decrease recovery time by allowing for increased mobility."

Disease, trauma and tumors affecting bones, such as vertebra, often require delivery of treatment agents, including therapeutic agents, to the area of the bone. Systems constructed in accordance with the principles herein provide a simple mechanism for combining bone stabilization, repair and/or replacement with treatment agent delivery to selected regions and/or to the entire surgical site as well as drainage pathways during and after the procedure.

Further, systems constructed in accordance with the principles herein can provide sustained, regulated, intermittent, and or evenly distributed substances spanning the entire posterolateral fusion without requiring or reducing the frequency of procedural reopening of the wound.

In addition, systems constructed in accordance with the principles herein provide the ability to customize the delivery location and amount of substance delivered during the course of an operation, once the bone rod is in place, for example. At the discretion of the surgeon, one or more drains can now be placed subcutaneously but also stably at the fusion site for the drainage and diagnostics of fluid. These benefits may reduce complications such as postoperative infections and seromas, for example.

Thus, systems constructed in accordance with the principles herein enable readjustment or realignment of the bone rod after initial spinal fixation, and can provide directed delivery of one or more substances during the procedure or at a later point in time. Bone rod constructed in accordance with the principles of the present disclosure thus allow one to selectively maintain a substance delivery pathway to one or more bone rod fenestrations. The bone rod fenestrations can be customized to facilitate regional treatments or surgical site treatments with needed substances, as desired.

Fluid delivery directly to a surgical site during a surgical procedure is facilitated due to the diameter of the cannula, and as such might decrease the incidence of subcutaneous tissue infections or increase the rate of bony fusion, for example. Other possible benefits include a better method for long-term, localized, controlled chemotherapeutic drug delivery for bony tumors located in posterolateral portion of vertebrae, which may reduce recurrence of aggressive tumors and/or provide further symptom relief.

One or more surgical site drainage pathways can be achieved in accordance with the principles herein. To this end, liquids and other mixed fluids may pass through one or multiple bone rod fenestrations into the fluid chamber and, through a negative pressure device or gravity, empty through attached flexible tubing into an external reservoir. Thus, the need for surgical debridement of the wound and rate of postoperative infections and seroma formation can be decreased in accordance with the principles herein.

BRIEF DESCRIPTION OF THE DRAWINGS

FIG. 3a shows a magnification of the site of attachment between the cannula and the bone rod fenestration. FIG. 3b shows a cross-sectional view of the site of attachment between the cannula and the bone rod fenestration.

FIG. 5a shows a perspective view of a cannula, or flexible tubing, and subcutaneous reservoir attached to a bone rod that is fixated to two cervical vertebrae along two pedicle screws.

FIG. 5b shows a lateral view of a cannula, or flexible tubing, and subcutaneous reservoir attached to a bone rod that is fixated to two cervical vertebrae along two pedicle screws. In accordance with this embodiment custom medications, such as chemotherapy delivered via a first rod and antibiotic formula delivered via the second rod are achievable in accordance with the principles herein.

FIG. 5c shows a superior view of a cannula, or flexible tubing, and subcutaneous reservoir attached to a bone rod that is fixated to two cervical vertebrae along two pedicle screws.

DETAILED DESCRIPTION OF THE PREFERRED EMBODIMENTS

Figures 1A, 1B, 1C:
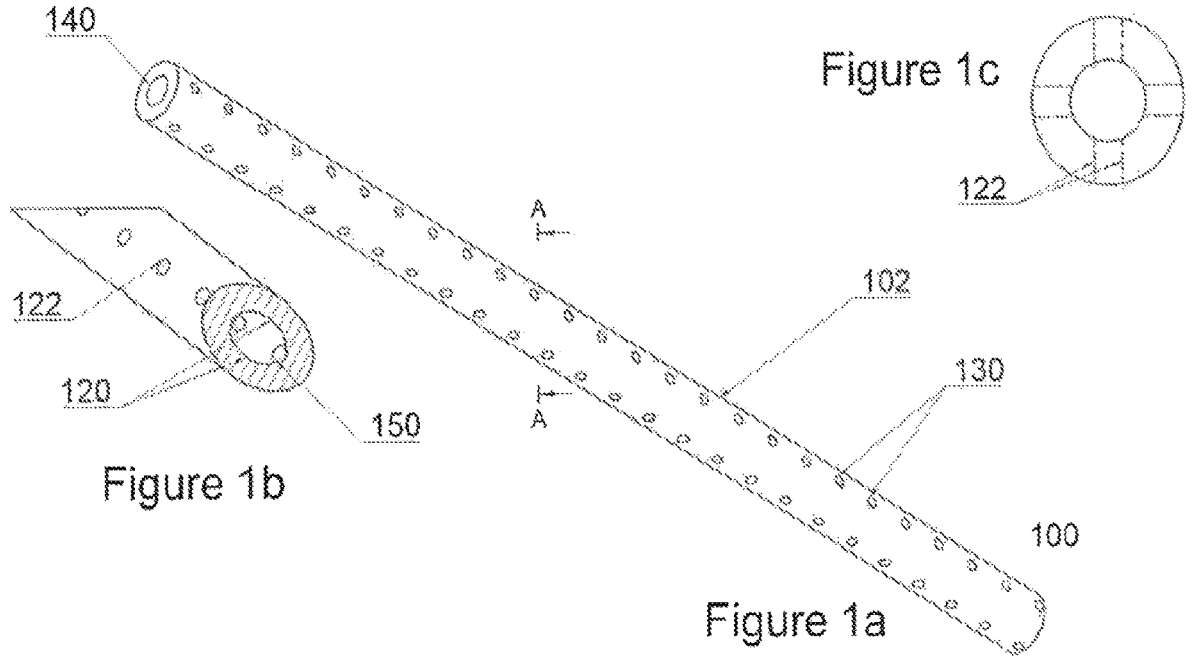
FIG. 1a shows a perspective view of a fenestrated bone rod in accordance with the present disclosure.
FIG. 1b shows a perspective cross-sectional view of a fenestrated bone rod.
FIG. 1c shows a superior cross-sectional view of a fenestrated bone rod.

In accordance with the present disclosure, a fenestrated bone rod can be configured as needed to deliver desired substances to the posterolateral fusion and/or to drain substances therefrom. The bone rod can be used to align two or more bones or bone pieces in a fixed spatial relationship with respect to each other. The bone rod can be cannulated along its entire length, or selected portion(s) thereof, thus creating a fluid chamber that connects all fenestrations.

Suitable substances that can be delivered via the system can include medicants or therapeutics, or other suitable substances which are desirable to deliver to the vicinity of a bone and surrounding tissue. For example, suitable substances can include antibiotics, chemotherapeutics, analgesics, and osteoinductives such as bone morphogenic protein, PMMA bone cement, or other substances. The substance or combination of substances can be delivered to the exterior of a bone, to the fracture interface between two or more broken bones, to the surrounding tissue around bone, or to any other location which may be facilitated for delivery of substances in accordance with the principles of the present disclosure.

Definitions: the term "cannulated" herein means that the rod comprises a hollow cavity, or fluid chamber, disposed inside a portion of or the entire length of its shaft, and a thin tube may be securely and removably inserted through an opening into fluid communication with the hollow cavity. The cavity consists of a bore beginning at one end of the rod and extending longitudinally along the rod, thus creating openings at each end of the rod. These additional openings may aid in establishing bony fusion between the bone rod and adjacent bone or bone fragments when bone morphogenic protein is delivered. Many configurations are possible, however, as the hollow cavity need not be restricted to a cylindrical shape or a circular cross-section.

The shape and size of the cavity may be suitably chosen to allow delivery of the desired substance through the rod to the bone area of interest. The cavity may be made as large as possible, so long as the rod maintains the structural integrity needed for fixation and spinal stability. The term "fenestration" herein is used broadly to include any slot, gap, or perforation that defines an opening between the inside of the cannulated portion of the rod to the outside of the rod, whereby a desired substance may be delivered and/or a fluid may be drained. Thus, a fenestrated rod comprises an opening which defines a substance delivery pathway between the internal cannulated portion and the exterior of the rod. In accordance with the present disclosure, fenestrations may typically be distributed evenly along the bone rod and distributed evenly in all directions, but other configurations are possible, depending on clinical use and discretion of the clinician. For example, fenestrations may only be provided on one side or direction of the rod, so as to facilitate targeted delivery of substances to and/or drainage of fluids from regions in one direction relative to the rod, e.g., to a region lateral to the spinal column to which the bone rod is affixed.

Any number or combination of fenestrations of one or more sizes can be located along the shaft, or at the ends of the rods, so long as the risk of rod fracture is not significantly increased. Further, in accordance with the present disclosure, the fenestrations may be any shape or size desired to facilitate delivery of the desired substance, and all fenestrations can be operational for cannulation. For example, the fenestration cross-sections may be round, oval, or square. The fenestration cross sections can change in diameter, if desired, between the inside and the outside of the rod to increase or decrease the flow rate of the substance and/or to facilitate removably connecting a cannula, tubing, and/or connector thereof to the fenestration(s).

As used herein, "bone rod" is defined by rods of all types that are presently known and modified in accordance with the principles herein or hereafter devised for fixation between bones and/or bone fragments and incorporating the features and advantages of the present disclosure. Such a bone rod may be substantially straight or may be curved, e.g., to match a curvature of a spine. The shape and dimensions of the bone rod may be modified according to a particular application and/or a bone rod having a particular shape and dimension may be selected, from a set of different bone rods, according to the particular application. For example, the length of the bone rod could be matched to a length of a site of spinal fusion of a patient, e.g., by cutting a longer bone rod to the specified length and/or selecting the bone rod from a set of bone rods that vary with respect to length. In some examples, the location and other properties of the fenestrations may be specified for a particular patient, e.g., to provide fenestrations only at locations that will be, subsequent to implantation of the bone rod, proximate to the bone screws, proximate to a region from which an osteoma has been removed, or proximate to some other target region relative to the implanted bone rod. This could include machining the fenestrations in the bone rod and/or using adhesive, screws, plugs, or other means to block fenestrations that are already present in a bone rod.

Note also that such a bone rod may be used to fix a first bone to a second bone or to fix other elements together. For example, such a fenestrated bone rod could be used to fix other bone rods (e.g., other fenestrated bone rods) to each other, e.g., to fix a first rod that is fixed, via bone screws, to the left of a spinal column to a second rod that is fixed, via different bone screws, to the right of the spinal column. In another example, such a fenestrated bone rod could be fixed to one or more bones (e.g., via bone screw(s)) and to one or more bone rods (e.g., one or more fenestrated bone rods) that may, themselves, be fixed to bone(s) and/or other bone rod(s).

Referring now to FIG. 1a, a system shown generally at 100 and including a bone rod 101 can also include a shaft 102. A cut-away of FIG. 1a reveals the system 100 includes a central fluid chamber 120 (FIG. 1b), and bone rod fenestrations 130 along the length of a fluid chamber 120. The fenestrations 130 need not be evenly spaced along the fluid chamber 120, but can be suitably arranged in a desired pattern or frequency along the length of the fluid chamber 120. Any fenestration 122 along the fluid chamber 120 of the bone rod 101 is configured to accept a thin tube insertion. This is intended as a non-limiting example embodiment; in some embodiments, only a subset of the fenestrations of a bone rod may be configured to accept a thin tube insertion (e.g., by being appropriately sized and shaped, by including ridges or other connection features).

In one exemplary embodiment the bone rod may be used to hold two or more bones or bone pieces in a fixed spatial relationship with respect to each other. Suitable rod sizes can be selected as needed for a given procedure. For example the bone rod can have a diameter in the range of 4 mm, such as bone rods typically used for posterolateral cervical fusion procedures, while rods in the range of 5.5 mm in diameter can be selected for lumbar fusion procedures, but other sizes can be selected as needed.

Bone rods may be contoured with a rod bender to align with a specific curvature of the spine. The rod cannot exceed a combination of degree of curvature, number and size of fenestrations, depth and length of rod cannulation that promotes structural instability or fracture of the rod when inserted and fixated. Suitable connector(s) can be configured to enable removal of the tubing from the fenestrated rod by using hands and light force/pressure between rod and cannula prior to implantation (outside the body); using hands and light force/pressure between rod and cannula prior to implantation (inside the body if size of skin aperture permits) and/or using additional tools known by those skilled in the art (if aperture is small) (e.g. use of a trocar), or other removal of the connector from the rod by additional system components or configurations.

For subcutaneous tubing, additional surgical intervention would be required to expose the distal end of the cannula (that would be attached to a pump or reservoir). At this point, the distal end could be forcefully pulled, detaching the proximal end of the tube. However, for cutaneous tubing, surgical intervention is not required to remove and instead a simple pull with hands is sufficient to detach from end of cannula.

A connector that is coupled to the flexible tubing can be adapted in a variety of ways to facilitate removably coupling the tubing to the bone rod (e.g., to a fenestration of the bone rod). This can include adapting the connector to reduce a likelihood that the connector is torn away from the tubing and/or that portions of the connector are broken off during the process of removing the connector from the bone rod. The presence of the connector and/or portions thereof following removal of the tubing is generally unwanted, as the remnant connector fragment(s) can lead to discomfort, infection, difficulties in performing revision procedures, or other unwanted effects, potentially necessitating an additional procedure to remove the connector fragments. These adaptations can have the functional result of making the force necessary to decouple the connector from the bone rod less then (e.g., less than a specified fraction of) a characteristic force sufficient to decouple (e.g. tear, fracture, detach an adhesive of) the connector from the tubing and/or to cause fracturing or other damage to the connector and/or the tubing itself.

In some examples, the connector could include one or more lips configured to retain the connector within a fenestration or other port or feature of the bone rod and to be subsequently removed therefrom (e.g., as in FIGS. 2a, 2b, 3, and 7). Such a connector could include slots or other features to control a force necessary to decouple the connector from the bone rod, so as to reduce the likelihood that the lip, a portion thereof, or any other portion of the connector is broken off during the process of removing the connector/ tubing from the bone rod). Such a connector, or a differently configured connector, could include one or more additional lips to prevent the connector from being inserted too far into the bone rod (e.g., thereby restricting the flow of fluids into/out of the tubing and out of/into the interior chamber(s) of the bone rod).

In some examples, the connector could be secured into a fenestration using an adhesive and/or secured onto the bone rod, bone screw(s), and/or associated tissues using sutures, an adhesive, clips, clamps, or other means. Such adhering means could be wholly or partially resorbable and/or could include features that soften and/or weaken over time (e.g., due to absorption of water from surrounding tissues, due to dissolution, enzymatic breakdown, or other processes resulting in breakdown and/or efflux of strengthening elements of the adhering means). Such resorption and/or weakening could result in the force necessary to decouple the connector and/or tubing from the bone rod reducing over time, thereby reducing the likelihood that, at a date days, weeks, or months after installation of the bone rod and tubing, the connector, tubing, and/or portions thereof are broken off during removal of the connector and tubing from a patient.

In some examples, the connector could be press-fitted into a fenestration, being thereby held into place by friction forces exerted between compressed elements of the connector and the internal surfaces of a fenestration or other port of the bone rod. In some examples, components of such a connector could dissolve, soften, or otherwise weaken over time, facilitating removal of the connector at a later date without resulting in any portions of the connector and/or tubing breaking off during removal of the connector and tubing from the body of a patient.

In some examples, the connector could be held in place by one or more magnets and/or magnetizable poles or elements. For example, the connector could include one or more magnets configured to exert an attractive force onto ferromagnetic or paramagnetic elements (e.g., iron alloy poles adhered to and/or formed within titanium or other nonmagnetic elements of the bone rod) of the bone rod.

In accordance with the present disclosure, the bone rod can be used to fuse vertebrae, to augment posterolateral fusion of vertebrae through delivery of osteoinductive growth factors, to deliver antibiotic drugs for prophylaxis treatment of postoperative infections, to promote mobility through delivery of analgesics, to deliver chemotherapy for reduction of tumor recurrence, and as a point of drainage for subcutaneous fluid through an attached cannula, or any combination of these, for example.

Other beneficial uses of bone rods are contemplated. For example, bone rods constructed in accordance with the principles herein can include any material suitable for placement into a bone without harmful effects on the patient. Examples of suitable materials include, but are not limited to, titanium and its alloys, tantalum and its alloys, nickel-cadmium and its alloys, steel and its alloys, plastics, absorbable materials, resorbable materials, polyamino acids, poly-lactide, polyglycolide, hydroxylapatite, and tricalciumphosphate, carbon fiber, and carbon fiber-alloy combinations. Other materials useful for bone rods construction are contemplated within the scope of the present disclosure.

Figures 2A, 2B:
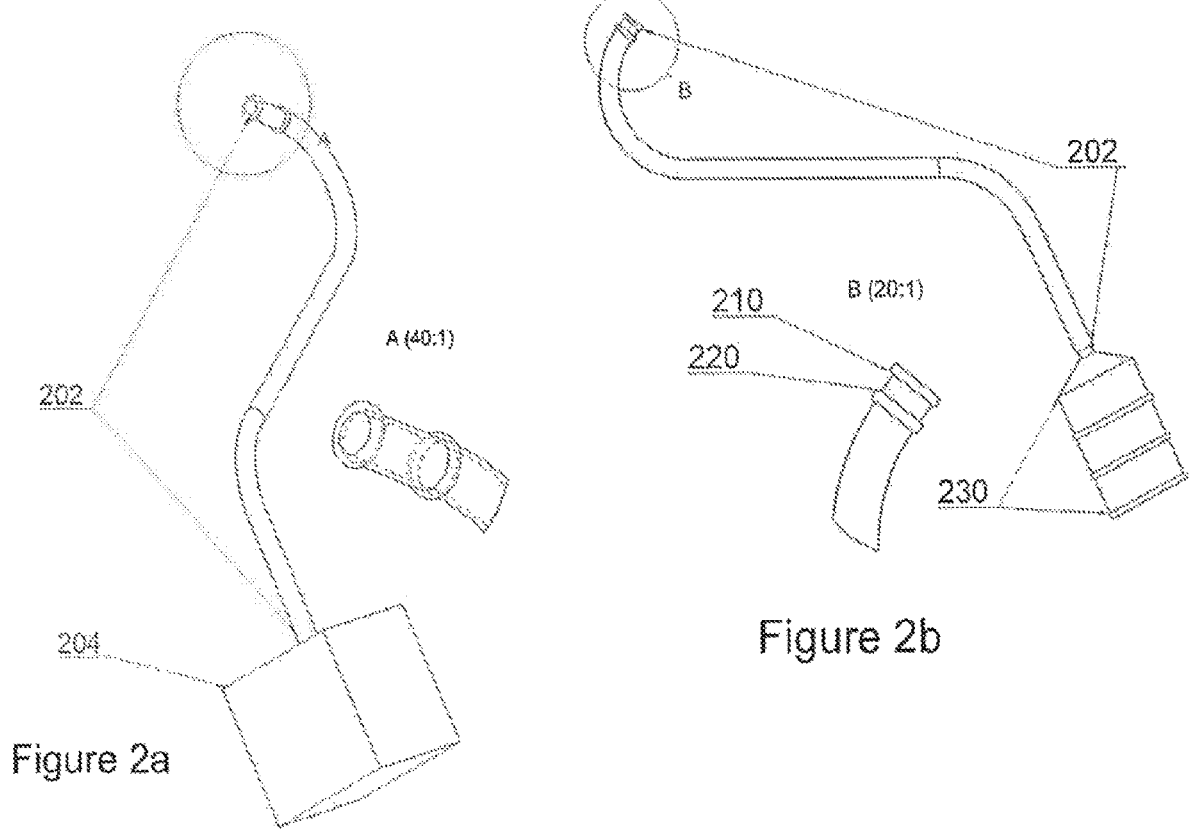
FIG. 2a shows a perspective view of a cannula, or flexible tubing, and attached subcutaneous reservoir, in accordance with the present disclosure.
FIG. 2b shows a lateral view of a cannula, or flexible tubing, and attached subcutaneous reservoir.

FIG. 2a and FIG. 2b are examples of a suitable cannula 202, or flexible tubing, for insertion into any bone rod fenestration for fluid delivery or drainage. However, other variations of tubing may be useful in accordance with the principles herein. For example, the subcutaneous cannula can be made of a polymer or another material suitable for implantation and fluid delivery while maintaining a required degree of flexibility. An end 204 of the cannula 202 can have an increased thickening 210, or annular ridge, at the most distant point.

Figure 3:
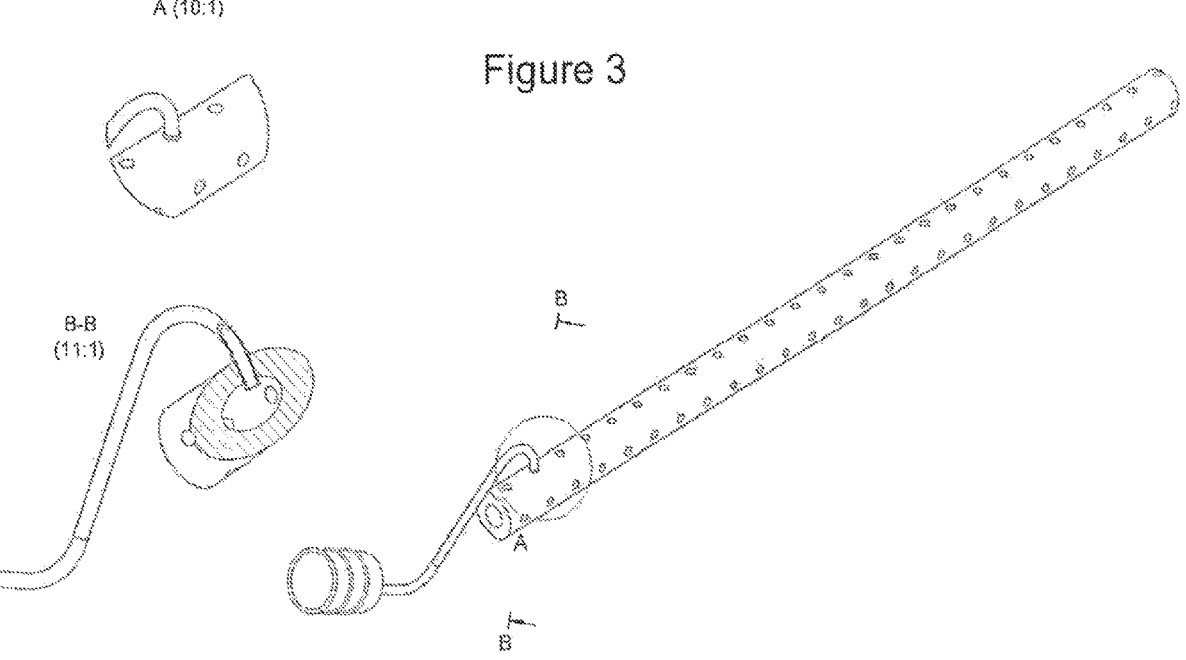
FIG. 3 shows a perspective view of a cannula, or flexible tubing, and a subcutaneous reservoir attached to a fenestrated bone rod.

The thickening 210 at the end 204 can be larger in diameter than the fenestration 122 into which the cannula 202 is selectively and removably inserted. The cannula 202 can be configured such that a minimal pressure will be required for the increased thickening 210 to pass into the fluid chamber of the rod, or the interior of the rod. A second thickening 220, or annular ridge, on the subcutaneous portion of the cannula may be present in close proximity to the first thickening, with some distance 0.5 mm to 7.0 mm between both thickenings. These two thickening may hold the cannula attached to the internal portion of the bone rod, as depicted in FIG. 3. Multiple additional thickenings may be present proximal to the first two thickenings in order to facilitate long term fixation and prevent subcutaneous displacement of the cannula. Fluid can be delivered to the patient via the system to treat or improve recovery to tissues at the site of a posterolateral fusion such as: vertebral bone features, such as facets, pedicles, transverse processes, bodies, laminae; connective tissue; adjacent muscle; fat tissue; anything else specific to a spinal fusion matrix, such as instruments or other biological tissue; and treatments such as osteoinductive bactericidal matrix, and any other previously delivered fluid to the site.

The second thickening 220 may be larger in diameter than the first thickening 210 in order to maintain fixation of the cannula 202 with the fenestration 122 into which it inserts. In certain applications of the present disclosure it may be desirable that the substance be stored in a reservoir prior to delivery to the external bone and surrounding tissue which comprises the posterolateral fusion.

Thus, it may be advantageous for the device of the present disclosure to further comprise a reservoir. For the purposes of this disclosure, the term "reservoir" refers to any source of the one or more substances to be delivered to the posterolateral fusion. When reservoir space is desired, a suitable reservoir may be connected to the cannula. For example the reservoir may constitute a pump 230 or micro-infusion device, as depicted in FIG. 2b, which connects directly with the cannula 202, or flexible tubing. A pump may be utilized to aid in delivery of the substance to the posterolateral fusion by, for example, delivering a continuous, regulated, or long-term volume to the rod. The pump may also be used to increase the fluid pressure within the cannulated portion of the rod, thereby aiding fluid flow through the rod fenestrations, for example. This embodiment may have the further advantage that the positive pressure created by the pump through the cannulated portion of the bone rod hampers the influx of unwanted materials or compounds into the bone rod. The cannula may be attached to an external reservoir or a subcutaneous reservoir 230, in which case the entire cannula may be subcutaneously implanted. The pump may be connected to the cannulated portion of the bone rod as depicted in FIGS. 2 and 3. Any suitable implantable pump or simple pump, such as external pumps similar to those used with patient controlled anesthesia machines or IV pumps can be connectable to components of the system.

Figure 4:
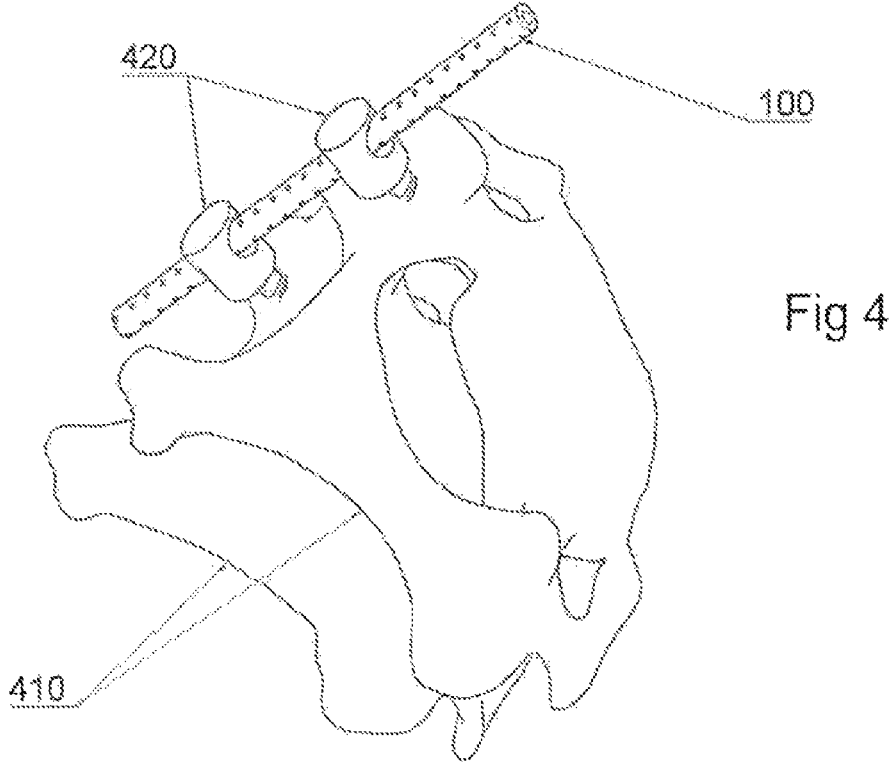
FIG. 4 shows a perspective view of a bone rod fixated to two cervical vertebrae along two pedicle screws.

As depicted in FIGS. 4, 5a and 5b, the bone rod 100 may stabilize two or more vertebrae 410, or bony structures, by fixating the rod with two or more pedicle screws 420. FIGS. 5a and 5b depict the same spinal fixation system along with flexible tubing 202 and subcutaneous reservoir 230 attached to the bone rod. In other instances, one end of this cannula may remain exterior to the body to facilitate a method for drainage of the surgical site. Any suitable tubing having sections thereof for subcutaneous drainage can be provided for subcutaneous components of the system. The tubing may be extendable and/or interchanged via a port or reservoir, if desired.

Figure 6:
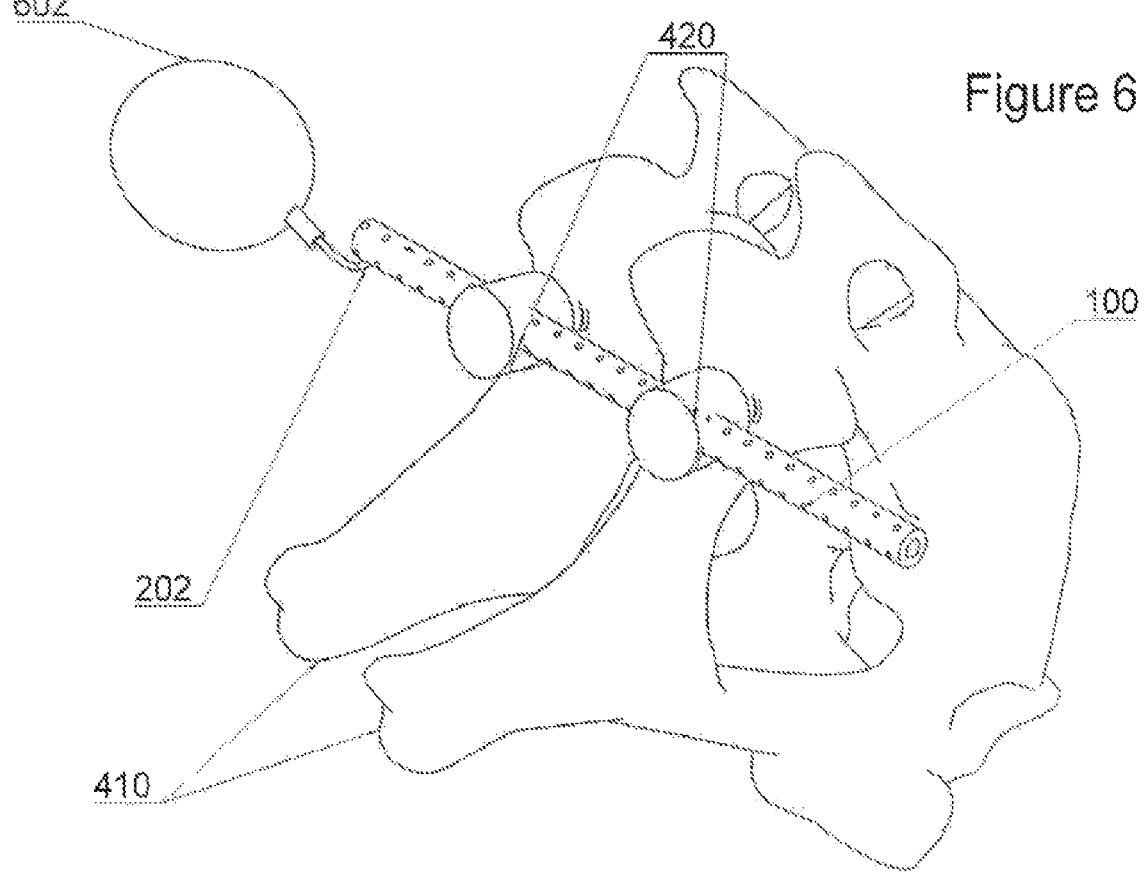
FIG. 6 shows a perspective view of a drain and cannula attached to a bone rod that is fixated to two cervical vertebrae along two pedicle screws.
Figure 7:
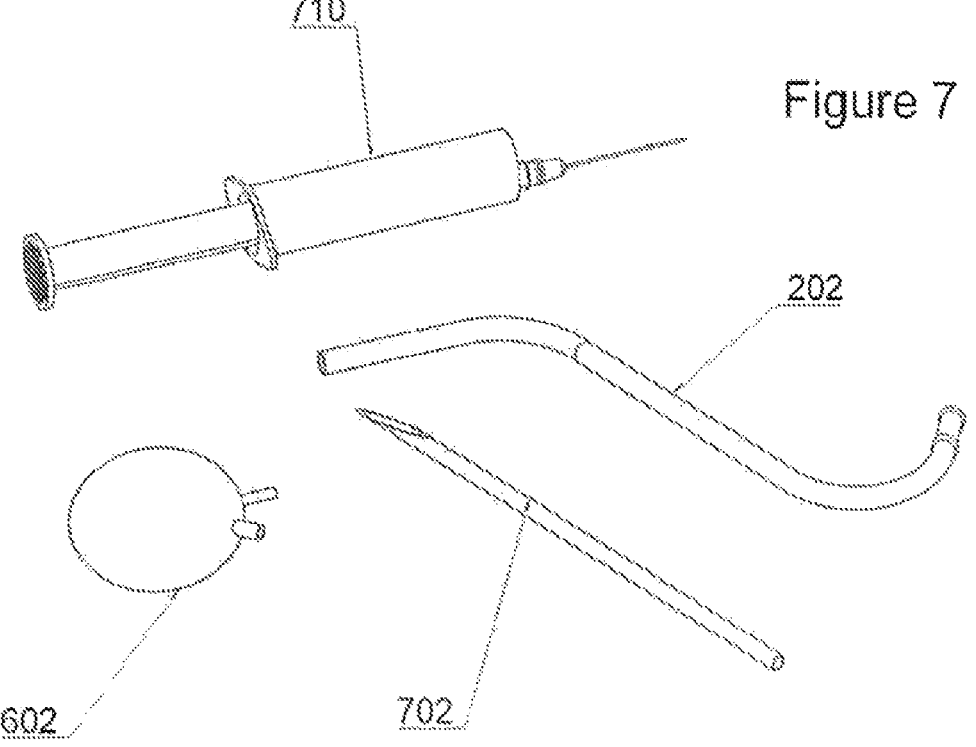
FIG. 7 shows a superior view of a cannula, drain, syringe, and trocar.
Figure 8:
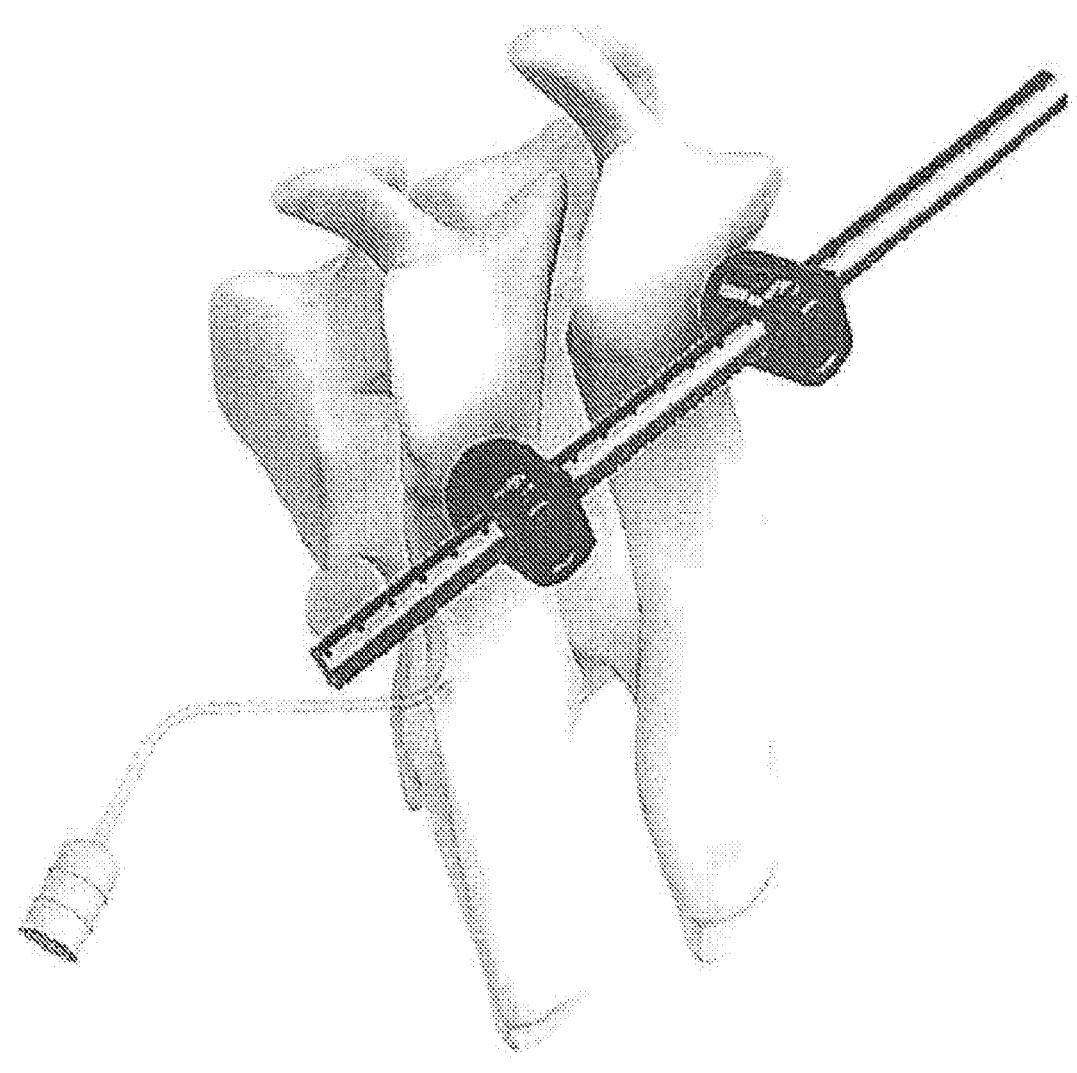
FIG. 8 illustrates an embodiment of a system constructed in accordance with the principles herein, wherein a tubing and reservoir are connectable to a fenestration-rod.

As depicted in FIG. 6, a method exists in which the cannula 202 and bone rod 100 together may act as a point of drainage for the entire posterolateral fusion. This may be accomplished by attaching one end of the cannula to a closed suction medical device FIG. 602. One such device is known to those skilled in the art as a Jackson-Pratt drain, however other devices may be used. This drain utilizes constant suction as a negative pressure system in order to pull fluid into a flexible bulb. A trocar 702, as depicted in FIG. 6, may be used to introduce the cannula near the posterolateral fusion through small skin apertures. In other instances known by those skilled in the art, a syringe may be preferred for the delivery of solution to the posterolateral fusion. A solution may be injected from the syringe 710—one example depicted in FIG. 7—into the transcutaneous end of the cannula or directly into one of the bone rod fenestrations. In both instances, the solution would be introduced into the fluid chamber of the bone rod and subsequently out of its fenestrations to the posterolateral fusion.

The present disclosure may further comprise the method of holding or fixing two or more bones or bone pieces in a fixed spatial relationship with respect to each other. Such a method may be desirable when delivering a substance such as a medicant or therapeutic to the vicinity where vertebral fractures are mended, a spondylolisthesis is repaired, or vertebrae are fused after a disc herniation, for example. Utilizing this method, a delivery pathway exists in which bone morphogenic protein may be injected into the fluid chamber 120 (FIG. 1) of the bone rod 100 and flow through its suitably sized and located fenestrations 130, its superior opening 140 and its inferior opening 150 onto bone. The stimulatory effects of the bone morphogenic protein may allow for the creation of a bone-rod interface that can improve stability of the vertebral fusion. Further modifications and alternative embodiments of various aspects of the disclosure will be apparent to those skilled in the art in view of this description. Accordingly, this description is to be construed as illustrative only.

The composition, dimensions, shape, number, and shape, size, and distribution of fenestrations of a bone rod as described herein may be specified in order to provide desired mechanical properties, osseointegration or other properties of biocompatibility, fluid flow properties, or other desired properties according to an application. For example, a bone rod may have a diameter between 3.3 and 4.5 millimeters when used to effect fusion of cervical vertebrae or between 5.5 and 6.5 millimeters when used to effect fusion of lumbar vertebrae. The interior/fluid chamber of such a bone rod may have a diameter between 0.5 and 1.5 millimeters. The diameter of a cannula, flexible tubing, trocar, needle, or other means used to deliver fluid into and/or receive fluid from the interior/fluid chamber of such a bone rod may have a diameter between 0.5 and 1.5 millimeters.

The construction and arrangements of the bone rod, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, or method steps may be varied or re-sequenced according to alternative embodiments. Other substitutions, modifications, changes and omissions may also be made in the design, operating conditions and arrangement of the various exemplary embodiments without departing from the scope of the present disclosure.

The invention claimed is:

1. A system for selectively connecting drainage and/or medicament pathways to a bone rod comprising:
   a removable connector configured to selectively connect to the bone rod, thereby securing the removable connector to the bone rod unless subjected to removal forces that exceed a first characteristic force, wherein the removable connector is configured to selectively connect to the bone rod via at least one of an annular ridge, one or more lips, an adhesive, one or more clips, one or more clamps, sutures, or press-fitting such that the first characteristic force is a non-zero force; and
   a flexible tubing connected to the removable connector to form a pathway for delivering medicaments or removing fluid in a region of the bone rod, wherein the first characteristic force is less than a specified fraction of a second characteristic force sufficient to separate the connector from the flexible tubing.

2. The system of claim 1, further comprising one or more fenestrations formed in the bone rod, the one or more connectors configured to provide a removable connection with the bone rod via the one or more fenestrations.

3. The system of claim 1, further comprising a pump connectable to the flexible tubing for delivering medicament to the bone rod or remove fluid from the bone rod.

4. A kit of components for assembling an implantable device, the kit comprising:
   a bone rod, wherein the bone rod has an interior chamber that extends along at least a portion of the length of the bone rod, and wherein the bone rod has a plurality of fenestrations extending from the interior chamber to an external surface of the bone rod; and a flexible tubing that is configured to be removably coupled to the bone rod, wherein the flexible tubing is configured to be in fluid communication with the interior chamber of the bone rod when removably coupled to the bone rod; and a connector coupled to the flexible tubing, wherein the flexible tubing is configured to be removably coupled to the bone rod via the connector, thereby securing the connector to the bone rod unless subjected to a removal force that exceeds a first characteristic force, wherein the removable connector is configured to selectively connect to the bone rod via at least one of an annular ridge, one or more lips, an adhesive, one or more clips, one or more clamps, sutures, or press-fitting such that the first characteristic force is a non-zero force, and wherein the first characteristic force is less than a specified fraction of a second characteristic force sufficient to separate the connector from the flexible tubing.

5. The kit of claim 4, further comprising:

two or more bone screws, wherein the two or more bone screws are configured to be fixed into bone, and wherein the two or more bone screws are configured to be fixed to the bone rod.

6. The kit of claim 4, wherein the interior chamber extends along the entire length of the bone rod.

7. The kit of claim 4, wherein the plurality of fenestrations are disposed along one side of the bone rod relative to a long axis of the bone rod.

8. The kit of claim 4, wherein the connector is configured to be removably coupled to the bone rod by being at least partially disposed within a particular fenestration of the plurality of fenestrations.

9. The kit of claim 8, wherein the connector comprises an inner lip configured to retain the connector within the particular fenestration when the connector is at least partially disposed within the particular fenestration.

10. The kit of claim 8, wherein the connector is configured to be retained within the particular fenestration, when the connector is at least partially disposed within the particular fenestration, by being press-fitted in the particular fenestration.

11. The kit of claim 10, wherein a portion of the connector is at least one of dissolvable or composed of a material that weakens over time.

12. The kit of claim 4, further comprising:

a reservoir that is configured to be attached to the flexible tubing such that the reservoir is in fluid communication with the flexible tubing.

13. A method comprising:

during a surgical intervention, fixing two or more bone screws into respective portions of bone of a patient;

during the surgical intervention, fixing a bone rod to the two or more bone screws, wherein the bone rod has an interior chamber that extends along at least a portion of the length of the bone rod, and wherein the bone rod has a plurality of fenestrations extending from the interior chamber to an external surface of the bone rod;

during the surgical intervention, coupling a flexible tubing to the bone rod such that the flexible tubing is in fluid communication with the interior chamber of the bone rod, wherein a connector is coupled to the flexible tubing, wherein coupling the flexible tubing to the bone rod comprises removably coupling the flexible tubing to the bone rod via the connector such that the connector is secured to the bone rod; and subsequent to an end of the surgical intervention, removing the flexible tubing from the patient by applying, to the flexible tubing, a force that is greater than a first characteristic force sufficient to uncouple the connector from the bone rod and that is less than a second characteristic force sufficient to separate the connector from the flexible tubing, thereby uncoupling the connector from the bone rod, wherein removably coupling the flexible tubing to the bone rod via the connector comprises using an adhesive, a suture, a clip, or a clamp to secure the connector to the bone rod, and wherein a portion of the adhesive, suture, clip, or clamp are at least one of resorbable or composed of a material that weakens over time such that a force sufficient to uncouple the connector from the bone rod decreases over time after coupling the flexible tubing to the bone rod via the connector.

14. The method of claim 13, wherein the plurality of fenestrations are disposed along one side of the bone rod relative to a long axis of the bone rod, wherein the two or more bone screws are fixed into respective portions of bone of a spinal column of the patient, and wherein fixing the bone rod to the two or more bone screws comprises fixing the bone rod to the two or more bone screws such that the plurality of fenestrations are directed away from the spinal column.

15. The method of claim 13, wherein removably coupling the flexible tubing to the bone rod comprises disposing the connector at least partially within a particular fenestration of the plurality of fenestrations.

16. The method of claim 13, further comprising:

providing medicament to tissues of the patient via the flexible tubing, the interior chamber, and at least a portion of the plurality of fenestrations, wherein the medicament is provided from a reservoir that is in fluid communication with the flexible tubing.

17. The method of claim 13, further comprising:

draining fluid from the patient via the flexible tubing, the interior chamber, and at least a portion of the plurality of fenestrations.

18. The method of claim 13, further comprising:

providing medicament to tissues of the patient via the interior chamber and at least a portion of the plurality of fenestrations, wherein the medicament is provided from a reservoir via a needle or trocar that is penetrating tissues of the patient and that is in fluid communication with at least one of the fenestrations.

19. The method of claim 13, further comprising:

draining fluid from the patient via the interior chamber and at least a portion of the plurality of fenestrations, wherein the fluid is drained via a needle or trocar that is penetrating tissues of the patient and that is in fluid communication with at least one of the fenestrations.

* * * * *